(12) United States Patent
Jeanne-Rose

(10) Patent No.: US 9,359,501 B2
(45) Date of Patent: Jun. 7, 2016

(54) COATED ORGANIC PIGMENT AND COSMETIC COMPOSITION

(71) Applicant: L'OREAL, Paris (FR)

(72) Inventor: Valerie Jeanne-Rose, Argenteuil (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/402,480

(22) PCT Filed: Jun. 6, 2013

(86) PCT No.: PCT/FR2013/051286
§ 371 (c)(1),
(2) Date: Nov. 20, 2014

(87) PCT Pub. No.: WO2013/186462
PCT Pub. Date: Dec. 19, 2013

(65) Prior Publication Data
US 2015/0110842 A1    Apr. 23, 2015

Related U.S. Application Data

(60) Provisional application No. 61/668,249, filed on Jul. 5, 2012.

(30) Foreign Application Priority Data

Jun. 15, 2012 (FR) ..................... 12 55598

(51) Int. Cl.
| | | |
|---|---|---|
| C09B 67/00 | (2006.01) |
| A61K 8/58 | (2006.01) |
| C09B 67/08 | (2006.01) |
| A61K 8/02 | (2006.01) |
| A61Q 1/02 | (2006.01) |
| A61Q 19/00 | (2006.01) |
| A61Q 3/02 | (2006.01) |

(52) U.S. Cl.
CPC ........... *C09B 67/0004* (2013.01); *A61K 8/0241* (2013.01); *A61K 8/585* (2013.01); *A61Q 1/02* (2013.01); *A61Q 3/02* (2013.01); *A61Q 19/00* (2013.01); *A61K 2800/10* (2013.01); *A61K 2800/43* (2013.01); *A61K 2800/434* (2013.01); *A61K 2800/622* (2013.01)

(58) Field of Classification Search
CPC . A61K 8/585; A61K 8/0241; A61K 2800/10; A61K 2800/43; A61K 2800/434; A61K 2800/602; C09B 67/0004; A61Q 1/02; A61Q 3/02; A61Q 19/00
USPC ......... 106/402, 410, 412, 493, 494, 495, 496, 106/497, 498, 499
See application file for complete search history.

(56) References Cited

U.S. PATENT DOCUMENTS 5,166,032 A * 11/1992 Nakamura et al. ....... C03G 9/09
430/137
2002/0069790 A1  6/2002 Hayashi et al.
2007/0238257 A1 10/2007 Paar et al.
2008/0199523 A1  8/2008 Finnie et al.

FOREIGN PATENT DOCUMENTS

| FR | 2795949 A1 | 1/2001 |
| JP | 2001-11342 A * | 1/2001 |
| WO | WO 2009/120846 A2 * | 10/2009 |

* cited by examiner

*Primary Examiner* — Anthony J Green
(74) *Attorney, Agent, or Firm* — Polsinelli PC

(57) ABSTRACT

The invention relates to a process for preparing a coated organic pigment, comprising the following steps: a) an anhydrous mixture; (i) of an organic pigment and (ii) of a siliceous compound of formula $[R_1—O]_3Si—R_2$ (I); in which $R_1$ denotes a $C_1$-$C_4$ alkyl radical and $R_2$ denotes a $C_1$-$C_8$ alkyl radical, is prepared; b) the mixture is placed in contact with an aqueous composition comprising a surfactant chosen from ($C_8$-$C_{16}$)alkyl sulfate salts and oxyethylenated ($C_6$-$C_{10}$)alkylphenols comprising from 5 to 40 ethylene oxide units; c) the coated pigment in powder form is recovered. The invention also relates to a coated organic pigment obtained according to this process, and also to a cosmetic composition containing such a coated organic pigment. Use for making up keratin materials.

20 Claims, No Drawings

COATED ORGANIC PIGMENT AND COSMETIC COMPOSITION

CROSS REFERENCE TO RELATED APPLICATIONS

This application is a National Phase filing under 35 U.S.C. §371 of PCT/FR2013/051286 filed on Jun. 6, 2013; and this application claims priority to Application No. 1255598 filed in France on Jun. 15, 2012; and this application claims the benefit of U.S. Provisional Application No. 61/665,249 filed on May 7, 2012. The entire contents of each application are hereby incorporated by reference.

The present invention relates to a process for preparing a coated organic pigment, to a coated organic pigment obtained according to this process and to a cosmetic composition comprising such a coated organic pigment. The invention also relates to a process for making up keratin materials using said composition. The composition and the makeup process are suitable for keratin materials such as human skin, lips, hair, eyelashes, eyebrows and nails. The composition is especially in the form of a makeup product, in particular a nail varnish, a lip product, a body makeup product, a foundation, an eyeshadow, a face powder, an eyeliner, a concealer product or a mascara.

Makeup compositions generally contain dyestuffs to give the composition the desired color. Dyestuffs may be mineral or organic pigments. It is known that fluorescent dyes make it possible to obtain vivid and very luminous colors that are visible in particular under ultraviolet lighting.

A fluorescent compound is a compound that is capable of absorbing UV or visible radiation at a wavelength $_{abs}$ of between 250 and 800 nm and capable of re-emitting in the visible range at an emission wavelength $_{em}$ of between 400 and 800 nm.

In cosmetics, few fluorescent dyes are permitted in makeup (mention may be made of Red 21, Red 22, Red 27, Red 28, Orange 5 and Yellow 11), which limits the variety and accessibility to these types of pigments for formulating makeup products in varied shades while at the same time having particularly attractive fluorescence effects. Organic pigments trapped in a polyester matrix are known, such as the products sold by the company Dayglo under the reference Dermaglo, especially Dermaglo DG-R222, DG-R228, DG-R422, DG-R428 and DG-0205.

Moreover, it is known practice from the prior art to coat organic pigments with siliceous coatings.

U.S. Pat. No. 6,355,260 describes organic or mineral pigments whose surface is coated with a mineral compound such as a silicic acid polymer or a deposit obtained after hydrolysis of tetraethoxysilane, or alternatively a deposit of alumina.

The hydrolysis of tetraethoxysilane does not make it possible to reveal the fluorescence of the organic pigment.

EP-A-581 651 describes colored spherical particles comprising an organic or mineral pigment coated with a hydrated metal compound obtained by hydrolysis of an alkoxy metal compound. In Examples 1, 4, 6 and 7, pigments are treated by hydrolysis of tetraethoxysilane.

JP-A-2002-308716 describes an organic pigment Red 202 coated by hydrolysis of tetraethoxysilane.

JP-A-2002-309173 describes organic and mineral pigments coated with silica, obtained by hydrolysis of tetraethoxysilane.

A need exists for other coated organic pigments that have good fluorescence properties to make it possible to broaden the range of fluorescent pigments available for the formulation of makeup products.

The Applicant has discovered, surprisingly, that it is possible to enhance the fluorescence of organic pigments by coating these pigments according to a process using a particular siliceous compound. This process makes it possible to form an alkylated silica coating which gives the organic pigment thus coated good fluorescence properties, thus making it possible to obtain makeup products that have vivid and luminous shades. The makeup obtained with these pigments also has good coverage.

More precisely, a subject of the invention is a process for preparing a coated organic pigment, comprising the following steps:

a) an anhydrous mixture
(i) of an organic pigment and (ii) of a siliceous compound of formula (I):

$$[R_1\text{---}O]_3Si\text{---}R_2 \qquad (I)$$

in which $R_1$ denotes a $C_1$-$C_4$ alkyl radical and $R_2$ denotes a $C_1$-$C_8$ alkyl radical; is prepared, optionally in the presence of less than 9.5% by weight (or even in the absence) of tetra($C_1$-$C_4$) alkyl orthosilicate; and optionally (iii) of an oil;

b) said mixture is placed in contact with an aqueous composition comprising a surfactant chosen from ($C_8$-$C_{16}$)alkyl sulfate salts and oxyethylenated ($C_6$-$C_{10}$)alkylphenols comprising from 5 to 40 ethylene oxide units;

c) the coated pigment in powder form is recovered.

A subject of the invention is also a coated organic pigment that may be obtained according to the process as defined previously.

A subject of the invention is also an organic pigment coated with an alkylated silica coating as defined hereinbelow.

Another subject of the invention is a cosmetic composition, especially a makeup composition, comprising, in a cosmetically acceptable medium, at least one coated organic pigment as defined previously.

A subject of the invention is also a process for making up keratin materials, comprising the application to said keratin materials of a cosmetic composition as defined previously.

Particles comprising a hydrophobic dopant intended to be released are known from document US 2008/0 199 523. The dopant may be a fluorescent dye such as Solvent Blue 35 dye and Sudan Red dye. These dyes are fat-soluble and do not correspond to an organic pigment that is insoluble in oils such as isododecane, decamethylcyclopentasiloxane or $C_{12}$-$C_{15}$ alkyl benzoates. The particles are prepared by encapsulation of the dopant during the sol-gel polymerization of 3-aminopropyltriethoxysilane and of vinyltrimethoxysilane in water in the presence of surfactant PEG-9 nonylphenyl ether (Examples 7 and 8). Said document does not recommend performing the encapsulation of organic pigments that are insoluble in oils to improve their fluorescent properties and to obtain makeup products with vivid and luminous shades, which have good coverage.

The term "cosmetically acceptable medium" means a medium that is compatible with human keratin materials such as the skin, the lips, the hair, the eyelashes or the nails.

The term "organic pigment" means an organic pigment that is insoluble in water at 25° C., especially at a content of 1% by weight, and also insoluble in oils chosen from isododecane, decamethylcyclopentasiloxane and $C_{12}$-$C_{15}$ alkyl benzoates, such as the product sold under the name Finsolv TN by the company Innospec Active Chemicals, at 25° C., especially at a content of 1% by weight.

The organic pigments intended to be coated may be, for example:
cochineal carmine,
organic pigments of azo dyes, anthraquinone dyes, indigoid dyes, xanthene dyes, pyrene dyes, quinoline dyes, triphenylmethane dyes or fluoran dyes;
organic lakes or insoluble sodium, potassium, calcium, barium, aluminum, zirconium, strontium or titanium salts of acidic dyes such as azo, anthraquinone, indigoid, xanthene, pyrene, quinoline, triphenylmethane or fluoran dyes. These dyes generally comprise at least one carboxylic or sulfonic acid group.

The organic lake may also be supported by any compatible support such as a mineral support, for instance particles of alumina, of clay, of zirconia or of metal oxides, in particular of zinc oxide or of titanium oxide, of talc, of calcium carbonate or of barium sulfate. Preferably, the mineral support is chosen from alumina, titanium oxide and barium sulfate.

The organic lake may also be supported on a support such as rosin or aluminum benzoate.

Among the organic pigments, mention may be made of D&C Red No. 7.

Among the organic lakes, mention may be made in particular of those known under the following names:
D&C Red No. 2 Aluminum lake
D&C Red No. 3 Aluminum lake
D&C Red No. 4 Aluminum lake
D&C Red No. 6 Aluminum lake
D&C Red No. 6 Barium lake
D&C Red No. 6 Barium/Strontium lake
D&C Red No. 6 Strontium lake
D&C Red No. 6 Potassium lake
D&C Red No. 7 Aluminum lake
D&C Red No. 7 Barium lake
D&C Red No. 7 Calcium lake
D&C Red No. 7 Calcium/strontium lake
D&C Red No. 7 Zirconium lake
D&C Red No. 8 Sodium lake
D&C Red No. 9 Aluminum lake
D&C Red No. 9 Barium lake
D&C Red No. 9 Barium/Strontium lake
D&C Red No. 9 Zirconium lake
D&C Red No. 10 Sodium lake
D&C Red No. 19 Aluminum lake
D&C Red No. 19 Barium lake
D&C Red No. 19 Zirconium lake
D&C Red No. 21 Aluminum lake
D&C Red No. 21 Zirconium lake
D&C Red No. 22 Aluminum lake
D&C Red No. 27 Aluminum lake
D&C Red No. 27 Aluminum/Titanium/Zirconium lake
D&C Red No. 27 Barium lake
D&C Red No. 27 Calcium lake
D&C Red No. 27 Zirconium lake
D&C Red No. 28 Aluminum lake
D&C Red No. 30 lake
D&C Red No. 31 Calcium lake
D&C Red No. 33 Aluminum lake
D&C Red No. 34 Calcium lake
D&C Red No. 36 lake
D&C Red No. 40 Aluminum lake
D&C Blue No. 1 Aluminum lake
D&C Green No. 3 Aluminum lake
D&C Orange No. 4 Aluminum lake
D&C Orange No. 5 Aluminum lake
D&C Orange No. 5 Zirconium lake
D&C Orange No. 10 Aluminum lake
D&C Orange No. 17 Barium lake
D&C Yellow No. 5 Aluminum lake
D&C Yellow No. 5 Zirconium lake
D&C Yellow No. 6 Aluminum lake
D&C Yellow No. 7 Zirconium lake
D&C Yellow No. 10 Aluminum lake
FD&C Blue No. 1 Aluminum lake
FD&C Red No. 4 Aluminum lake
FD&C Red No. 40 Aluminum lake
FD&C Yellow No. 5 Aluminum lake
FD&C Yellow No. 6 Aluminum lake The chemical compounds corresponding to each of the organic pigments mentioned previously are mentioned in the publication *International Cosmetic Ingredient Dictionary and Handbook*, 1997 edition, pages 371 to 386 and 524 to 528, published by The Cosmetic, Toiletries and Fragrance Association.

Use may also be made of lakes of natural dyes such as lakes of curcumin, riboflavin, azorubin, amaranth or chlorophyll, of carotenoids such as lycopene, or of anthocyans, sorghum or carminic acid.

The siliceous compound of formula (I) described previously, used in the process according to the invention, makes it possible to form at the surface of the organic pigment a coating of alkyl silica type. This coating is obtained by hydrolysis and condensation of the siliceous compound (I), which takes place after contact with water.

In the siliceous compound (I), $R_1$ denotes a $C_1$-$C_4$ alkyl radical and $R_2$ denotes a $C_1$-$C_8$ alkyl radical. Preferably, $R_2$ denotes a $C_1$-$C_4$ alkyl radical.

For the siliceous compound (I) defined previously, advantageously, $R_1$ denotes a $C_2$-$C_3$ alkyl radical and $R_2$ denotes a $C_1$-$C_4$ alkyl radical.

Preferentially, $R_1$ is an ethyl radical and $R_2$ is a methyl radical.

The siliceous compound (I) may be chosen from methyltriethoxysilane, propyltrimethoxysilane and methyltrimethoxysilane.

Preferably, the siliceous compound (I) is methyltriethoxysilane.

The siliceous compound (I) forms, after hydrolysis and condensation, an alkyl silica network bearing repeating units of $(SiO_{3/2}R_2)$ type, $R_2$ denoting a $C_1$-$C_8$ alkyl group.

Thus, the pigment is coated with a coating comprising an alkyl silica bearing these repeating units.

The siliceous compound (I) may generally be present in a proportion of from 33% to 99.5% by weight, preferably in a proportion of from 50% to 86% by weight and most particularly in a proportion of from 55% to 70% by weight relative to the total weight of the anhydrous mixture.

The organic pigment may generally be present in a proportion of from 0.49% to 34% by weight, preferably in a proportion of from 5% to 30% by weight and most particularly in a proportion of from 10% to 15% by weight relative to the total weight of the anhydrous mixture.

Advantageously, the organic pigment and the siliceous compound (I) are used in the preparation process according to the invention in an organic pigment/siliceous compound (I) weight ratio ranging from 0.08 to 1 and preferably ranging from 0.3 to 0.8.

The oil optionally present in the anhydrous mixture may be chosen from oils that are common in cosmetics.

The oil is advantageously an apolar and especially volatile oil.

$C_{12}$ to $C_{15}$ alkyl benzoates may also be used as oil, such as those sold under the name Tegosoft TN from Evonik Goldschmidt.

For the purposes of the present invention, the term "apolar oil" is intended to mean an oil of which the solubility parameter at 25° C., $\delta_a$, is equal to 0 $(J/cm^3)^{1/2}$.

The definition and calculation of the solubility parameters in the Hansen three-dimensional solubility space are described in the article by C. M. Hansen: *The three-dimensional solubility parameters*, J. Paint Technol. 39, 105 (1967). According to this Hansen space:

- $\delta_D$ characterizes the London dispersion forces derived from the formation of dipoles induced during molecular impacts;
- $\delta_p$ characterizes the Debye interaction forces between permanent dipoles and also the Keesom interaction forces between induced dipoles and permanent dipoles;
- $\delta_h$ characterizes the specific interaction forces (such as hydrogen bonding, acid/base, donor/acceptor, etc.); and
- $\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

The term "apolar hydrocarbon-based oil" means an oil formed essentially from, or even constituted by, carbon and hydrogen atoms, and free of heteroatoms such as N, O, Si and P.

The apolar hydrocarbon-based oil may also be a volatile oil.

The term "volatile oil" means an oil that can evaporate on contact with the skin, at room temperature and atmospheric pressure. The volatile oils of the invention are volatile cosmetic oils, which are liquid at room temperature, having a nonzero vapor pressure, at room temperature and atmospheric pressure, ranging in particular from 0.13 Pa to 40 000 Pa (0.001 to 300 mmHg) and preferably ranging from 1.3 Pa to 1300 Pa (0.01 to 10 mmHg). Conversely, a nonvolatile oil has a vapor pressure of less than 0.13 Pa.

Examples of nonvolatile apolar hydrocarbon-based oils that may be mentioned include hydrocarbon-based oils, for instance squalene, linear or branched hydrocarbons such as liquid paraffin, liquid petroleum jelly and naphthalene oil, polybutene, polyisobutene, hydrogenated or partially hydrogenated polyisobutene, isoeicosane, squalane, decene/butene copolymers, polybutene/polyisobutene copolymers, especially Indopol L-14, and polydecenes such as Puresyn 10, and mixtures thereof.

In particular, mention may be made of nonvolatile hydrocarbon-based apolar oils of high molecular mass, also known as glossy oils, the molecular mass being, for example, between 650 and 10 000 g/mol, for instance:

- polybutylenes such as Indopol H-100 (molar mass or MW=965 g/mol), Indopol H-300 (MW=1340 g/mol) and Indopol H-1500 (MW=2160 g/mol) sold or manufactured by the company Amoco,
- hydrogenated polyisobutylenes such as Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol),
- polydecenes and hydrogenated polydecenes such as Puresyn 150 (MM=9200 g/mol) sold by the company Mobil Chemicals, and
- mixtures thereof.

Apolar hydrocarbon-based volatile oils that may be mentioned include hydrocarbon-based volatile oils containing from 7 to 16 carbon atoms, and mixtures thereof, and preferably from 8 to 16 carbon atoms, especially branched $C_8$-$C_{16}$ alkanes such as $C_8$-$C_{16}$ isoalkanes (also known as isoparaffins), isododecane, isodecane, isohexadecane and, for example, the oils sold under the trade names Isopar or Permethyl, and mixtures thereof.

According to one embodiment, the volatile or nonvolatile apolar oils that are suitable for use in the invention may be chosen from polybutene, polyisobutene, hydrogenated polyisobutene, isododecane and isohexadecane, and mixtures thereof.

Apolar hydrocarbon-based volatile oils that may be mentioned include hydrocarbon-based volatile oils containing from 7 to 15 carbon atoms and mixtures thereof, and especially linear $C_7$-$C_{15}$ alkanes.

Preferably, the "volatile linear alkanes" that are suitable for use in the invention comprise from 8 to 14 carbon atoms.

Preferably, the "volatile linear alkanes" that are suitable for use in the invention comprise from 9 to 14 carbon atoms.

Preferably, the "volatile linear alkanes" that are suitable for use in the invention comprise from 10 to 14 carbon atoms.

Preferably, the "volatile linear alkanes" that are suitable for use in the invention comprise from 11 to 14 carbon atoms.

The "volatile linear alkanes" that may be used in the compositions according to the invention may in particular have a nonzero vapor pressure (also known as the saturating vapor pressure), at room temperature, in particular a vapor pressure ranging from 0.3 Pa to 6000 Pa.

Preferably, the "volatile linear alkanes" that are suitable for use in the invention have a vapor pressure ranging from 0.3 to 2000 Pa, at room temperature (25° C.).

Preferably, the "volatile linear alkanes" that are suitable for use in the invention have a vapor pressure ranging from 0.3 to 1000 Pa, at room temperature (25° C.).

More preferably, the "volatile linear alkanes" that are suitable for use in the invention have a vapor pressure ranging from 0.4 to 600 Pa, at room temperature (25° C.).

Preferably, the "volatile linear alkanes" that are suitable for use in the invention have a vapor pressure ranging from 1 to 200 Pa, at room temperature (25° C.).

Even more preferably, the "volatile linear alkanes" that are suitable for use in the invention have a vapor pressure ranging from 3 to 60 Pa, at room temperature (25° C.).

As examples of alkanes that are suitable for use in the invention, mention may be made of the alkanes described in patent applications by the company Cognis WO 2007/068 371 or WO 2008/155 059 (mixtures of different alkanes differing by at least one carbon). These alkanes are obtained from fatty alcohols, which are themselves obtained from coconut oil or palm oil.

As examples of linear alkanes that are suitable for use in the invention, mention may be made of:
n-heptane (C7), n-octane (C8), n-nonane (C9), n-decane (C10), n-undecane (C11), n-dodecane (C12), n-tridecane (C13) and n-tetradecane (C14), and mixtures thereof. According to a particular embodiment, the volatile linear alkane is chosen from n-nonane, n-undecane, n-dodecane, n-tridecane and n-tetradecane, and mixtures thereof.

According to a preferred mode, mention may be made of mixtures of n-undecane (C11) and of n-tridecane (C13) obtained in Examples 1 and 2 of patent application WO 2008/155 059 from the company Cognis.

Mention may also be made of n-dodecane (C12) and n-tetradecane (C14) sold by Sasol under the references, respectively, Parafol 12-97 and Parafol 14-97, and also mixtures thereof.

The oil may be present in the anhydrous mixture in a content ranging from 0 to 60% by weight and preferably ranging from 5% to 50% by weight relative to the total weight of the anhydrous mixture.

The aqueous phase used in the preparation process according to the invention contains a surfactant as defined previously.

The surfactant may be chosen from $(C_8-C_{16})$alkyl sulfate salts, especially chosen from said sodium, potassium, magnesium and ammonium salts.

The surfactant is chosen in particular from $(C_{10}-C_{14})$alkyl sulfate salts, especially chosen from said sodium, potassium, magnesium and ammonium salts.

Preferentially, the surfactant is chosen from lauryl sulfate salts, especially chosen from said sodium, potassium, magnesium and ammonium salts.

Advantageously, the surfactant is sodium lauryl sulfate.

The surfactant may also be chosen from ethoxylated $(C_6-C_{10})$alkylphenols containing from 5 to 40 ethylene oxide units. Preferentially, the surfactant is chosen from ethoxylated octylphenol containing from 5 to 40 ethylene oxide units.

Surfactants that may be used include the following compounds:

Ethoxylated octylphenol containing 5 ethylene oxide units: INCI name Octoxynol-5; such as Triton X-45 from Dow Chemical Company Ethoxylated octylphenol containing 8 ethylene oxide units: INCI name Octoxynol-8; such as Triton X-114 from Dow Chemical Company Ethoxylated octylphenol containing 9 ethylene oxide units: INCI name Octoxynol-9; such as Triton X-100 from Dow Chemical Company Ethoxylated octylphenol containing 13 ethylene oxide units: INCI name Octoxynol-13; such as Triton X-102 from Dow Chemical Company Ethoxylated octylphenol containing 16 ethylene oxide units: INCI name Octoxynol-16; such as Triton X-165 from Dow Chemical Company Ethoxylated octylphenol containing 30 ethylene oxide units: INCI name Octoxynol-30; such as Triton X-305 from Dow Chemical Company Ethoxylated octylphenol containing 40 ethylene oxide units: INCI name Octoxynol-40; such as Triton X-405 from Dow Chemical Company Preferentially, ethoxylated octylphenol containing from 8 to 16 ethylene oxide units is used.

Advantageously, ethoxylated octylphenol containing 9 ethylene oxide units is used.

The surfactant may be present in the aqueous composition used in the preparation process in a content ranging from 0.1% to 5% by weight and preferably ranging from 0.2% to 1.5% by weight relative to the total weight of the aqueous composition.

The aqueous composition may comprise a nonionic water-soluble thickener, especially in a content ranging from 0.1% to 10% by weight relative to the total weight of the aqueous phase.

Among the nonionic water-soluble thickeners that may be used according to the invention, mention may be made of:
water-soluble cellulose-based thickeners, such as hydroxyethylcellulose, methylcellulose or hydroxypropylcellulose;
guar gum;
nonionic guar gums comprising $C_1-C_6$ hydroxyalkyl groups. Mention may be made, for example, of hydroxymethyl, hydroxyethyl, hydroxypropyl and hydroxybutyl groups. Such guar gums are especially sold under the trade names Jaguar HP8, Jaguar HP60, Jaguar HP120 and Jaguar HP105 by the company Meyhall, or under the name Galactasol 40H4FD2 by the company Aqualon;
xanthan gum, locust bean gum, scleroglucan gum, gellan gum;
polyvinylpyrrolidone;
polyvinyl alcohol.

Preferably, polyvinyl alcohol is used.

The process for preparing the coated organic pigment according to the invention comprises the following steps:
a) an anhydrous mixture
(i) of an organic pigment and (ii) of a siliceous compound of formula (I):

$$[R_1-O]_3Si-R_2 \qquad (I)$$

in which $R_1$ denotes a $C_1-C_4$ alkyl radical and $R_2$ denotes a $C_1-C_8$ alkyl radical; is prepared, optionally in the presence of less than 9.5% by weight (or even in the absence) of tetra($C_1-C_4$) alkyl orthosilicate;
and optionally of an oil;
b) said mixture is placed in contact with an aqueous composition comprising a surfactant chosen from $(C_8-C_{16})$alkyl sulfate salts and oxyethylenated $(C_6-C_{10})$alkylphenols comprising from 5 to 40 ethylene oxide units;
c) the coated pigment in powder form is recovered.

The final mixture may be left to act at a temperature ranging from 10° C. to 30° C., especially at room temperature (25° C.). Stirring of said mixture may last from 5 minutes to 1 hour. The product derived from the contact of the siliceous compound (I) with water deposits on the organic pigment and coats it, forming a coating of alkyl silica type.

The reaction medium may then be filtered or centrifuged and the collected filtrate is washed, especially with water. After drying, a powder is obtained.

In the process according to the invention, the final mixture, the organic pigment, the siliceous compound (I) and water, is advantageously stirred efficiently to prevent the formation of agglomerates and/or to deaggregate the agglomerates as they form. After reaction, a powder of coated organic pigment is thus obtained. According to a particular embodiment of the process according to the invention, said final mixture may be ultrasonicated to deaggregate the agglomerates that may form during the reaction.

The average size of the particles of coated organic pigment may range from 0.1 μm to 500 μm, preferably from 1 μm to 500 μm and preferentially from 1 μm to 100 μm.

The content of coating product in the coated organic pigment may range from 20% to 300% by weight relative to the weight of organic pigment (uncoated) and preferably from 80% to 150% by weight.

The coated organic pigment may be present in the cosmetic composition according to the invention in a content ranging from 0.1% to 99% by weight, preferably from 0.5% to 80% by weight and better still from 1% to 60% by weight relative to the total weight of the composition.

The cosmetic composition according to the invention may be in the form of a water-in-oil or oil-in-water emulsion, a loose or compacted powder, a cast powder, a solid stick, a paste or an organic or aqueous lotion.

The composition may also comprise other ingredients commonly used in cosmetic compositions. Such ingredients may be chosen from preserving agents, fragrances, sunscreens, oils, waxes, thickeners, film-forming polymers, moisturizers, vitamins, proteins, ceramides, surfactants, antioxidants, free-radical scavengers, organic solvents, water and mineral pigments.

Needless to say, a person skilled in the art will take care to select this or these optional additional compound(s), and/or the amount thereof, such that the advantageous properties of the composition according to the invention are not, or are not substantially, adversely affected by the envisaged addition.

The invention is illustrated in greater detail in the examples that follow.

EXAMPLE 1 a) Coated Organic Pigment 1.5 g of D&C Red No. 7 (INCI name CI 15850) were dispersed in 10 g of methyltriethoxysilane (MTES) to make an organic phase. 0.45 g of oxyethylenated octylphenol (9 ethylene oxide units) (Triton® X100 from Dow Chemical) was dissolved in 100 g of water. This aqueous phase was emulsified with the organic phase by means of a rotor-stator at 13 500 rpm for 10 minutes. At the end of emulsification, the emulsion was maintained under magnetic stirring, and 0.17 g of 0.1 M HCl was added. After 10 minutes, 0.21 g of 20% aqueous ammonia solution was added. The mixture was stirred for 24 hours and then centrifuged for 30 minutes at 4000 rpm, and then washed with water and centrifuged again. The powder obtained was recovered on filter paper and then air-dried.

The fluorescence of the coated pigment obtained was evaluated under a 365 nm UV lamp: the pigment has enhanced fluorescence.

EXAMPLE 2

0.56 g of D&C Red No. 7 (INCI name CI 15850) was dispersed in 10 g of methyltriethoxysilane to make an organic phase. 0.45 g of oxyethylenated octylphenol (9 ethylene oxide units) (Triton® X100 from Dow Chemical) was dissolved in 100 g of water. This aqueous phase was emulsified with the organic phase by means of a rotor-stator at 13 500 rpm for 10 minutes. At the end of emulsification, the emulsion was maintained under magnetic stirring, and 0.17 g of 0.1 M HCl was added. After 10 minutes, 0.21 g of 20% by weight aqueous ammonia solution was added. The mixture was stirred for 24 hours and then centrifuged for 30 minutes at 4000 rpm, and then washed with water and centrifuged again. The powder obtained was recovered on filter paper and then air-dried.

The fluorescence of the coated pigment obtained was evaluated under a 365 nm UV lamp, in comparison with that of the uncoated pigment: the coated pigment has enhanced fluorescence.

EXAMPLE 3

1.5 g of D&C Red No. 7 (INCI name CI 15850) were dispersed in 5 g of C12-C15 alkyl benzoate (Tegosoft TN from Evonik Goldschmidt) and 10 g of methyltriethoxysilane to make an organic phase. 0.42 g of oxyethylenated octylphenol (9 ethylene oxide units) (Triton® X100 from Dow Chemical) was dissolved in 100 g of water. This aqueous phase was emulsified with the organic phase by means of a rotor-stator at 13 500 rpm for 10 minutes. At the end of emulsification, the emulsion was maintained under magnetic stirring, and 0.17 g of 0.1 M HCl was added. After 10 minutes, 0.21 g of 20% by weight aqueous ammonia solution was added. The mixture was stirred for 24 hours and then centrifuged for 30 minutes at 4000 rpm, and then washed with water and centrifuged again. The powder obtained was recovered on filter paper and then air-dried.

The fluorescence of the coated pigment obtained was evaluated under a 365 nm UV lamp, in comparison with that of the uncoated pigment: the coated pigment has enhanced fluorescence.

EXAMPLE 4

2.52 g of D&C Red No. 7 (INCI name CI 15850) was dispersed in 23.7 g of methyltriethoxysilane and 0.84 g of isododecane to make an organic phase. 1.68 g of sodium lauryl ether sulfate were dissolved in 200 g of water containing 5% by weight of 98% hydrolyzed PVA (Mw=13 000–25 000) (Celvol® 305 from Celanese Chemicals).

The two phases were emulsified with a sonicator and the mixture was then stirred for 5 hours. The powder obtained was recovered by filtration on paper.

The fluorescence of the coated pigment obtained was evaluated under a 365 nm UV lamp, in comparison with that of the uncoated pigment: the coated pigment has enhanced fluorescence.

EXAMPLE 5

Outside the Invention 0.56 g of D&C Red No. 7 (INCI name CI 15850) was dispersed in 1 g of methyltriethoxysilane and 9 g of tetraethyl orthosilicate to make an organic phase. 0.45 g of oxyethylenated octylphenol (9 ethylene oxide units) (Triton® X100 from Dow Chemical) was dissolved in 100 g of water. This aqueous phase was emulsified with the organic phase by means of a rotor-stator at 13 500 rpm for 10 minutes. At the end of emulsification, the emulsion was maintained under magnetic stirring, and 0.17 g of 0.1 M HCl was added. After 10 minutes, 0.21 g of 20% $NH_3$ solution was added. The mixture was stirred for 24 hours and then centrifuged for 30 minutes at 4000 rpm, and then washed with water and centrifuged again. The powder obtained was recovered on filter paper and then air-dried.

The fluorescence of the coated pigment obtained was evaluated under a 365 nm UV lamp: the fluorescence is not enhanced in comparison with that of the uncoated pigment.

EXAMPLE 6

Outside the Invention 0.56 g of D&C Red No. 7 (INCI name CI 15850) was dispersed in 9 g of methyltriethoxysilane and 1 g of tetraethyl orthosilicate to make an organic phase. 0.45 g of oxyethylenated octylphenol (9 ethylene oxide units) (Triton® X100 from Dow Chemical) was dissolved in 100 g of water. This aqueous phase was emulsified with the organic phase by means of a rotor-stator at 13 500 rpm for 10 minutes. At the end of emulsification, the emulsion was maintained under magnetic stirring, and 0.17 g of 0.1 M HCl was added. After 10 minutes, 0.21 g of 20% $NH_3$ solution was added. The mixture was stirred for 24 hours and then centrifuged for 30 minutes at 4000 rpm, and then washed with water and centrifuged again. The powder obtained was recovered on filter paper and then air-dried.

The fluorescence of the coated pigment obtained was evaluated under a 365 nm UV lamp: the fluorescence is not enhanced in comparison with that of the uncoated pigment.

EXAMPLE 7

Outside the Invention 0.56 g of D&C Red No. 7 (INCI name CI 15850) was dispersed in 10 g of methyltriethoxysilane to make an organic phase. 0.45 g of a condensate of ethylene oxide and propylene oxide and ethylene oxide (75 EO/30 PO/75 EO) (Pluracare/Pluronic F 68 Prill from BASF) was dissolved in 100 g of water. This aqueous phase was emulsified with the organic phase by means of a rotor-stator at 13 500 rpm for 10 minutes. At the end of emulsification, the emulsion was maintained under magnetic stirring, and 0.17 g of 0.1 M HCl was added. After 10 minutes, 0.21 g of 20% $NH_3$ solution was added. The mixture was stirred for 24 hours. The mixture was stirred for 24 hours and then centrifuged for 30 minutes at 4000 rpm, and then washed with water and centrifuged again. The powder obtained was recovered on filter paper and then air-dried.

The fluorescence of the coated pigment obtained was evaluated under a 365 nm UV lamp: the fluorescence is not enhanced in comparison with that of the uncoated pigment.

EXAMPLE 8

Outside the Invention 1.5 g of D&C Red No. 7 (INCI name CI 15850) was dispersed in 10 g of methyltriethoxysilane to make an organic phase. 0.45 g of diester formed by reaction of octyldodecanol and of PPG-3 myristyl ether with dilinoleic acid (dimer) (INCI name: Octyldodecyl/PPG-3 myristyl ether dimer dilinoleate) (Liquiwax Polyefa OR from Arch Personal Care) was dissolved in 100 g of water. This aqueous phase was emulsified with the organic phase by means of a rotor-stator at 13 500 rpm for 10 minutes. At the end of emulsification, the emulsion was maintained under magnetic stirring, and 0.17 g of 0.1 M HCl was added. After 10 minutes, 0.21 g of 20% $NH_3$ solution was added. The mixture was stirred for 24 hours and then centrifuged for 30 minutes at 4000 rpm, and then washed with water and centrifuged again. The powder obtained was recovered on filter paper and then air-dried.

The fluorescence of the coated pigment obtained was evaluated under a 365 nm UV lamp: the fluorescence is not enhanced in comparison with that of the uncoated pigment.

EXAMPLE 9

Outside the Invention 0.56 g of D&C Red No. 7 (INCI name CI 15850) was dispersed in 10 g of methyltriethoxysilane to make an organic phase. 0.45 g of a condensate of ethylene oxide and propylene oxide and ethylene oxide (17 EO/60 PO/17 EO) (Pluronic P 103 from BASF) was dissolved in 100 g of water. This aqueous phase was emulsified with the organic phase by means of a rotor-stator at 13 500 rpm for 10 minutes. At the end of emulsification, the emulsion was maintained under magnetic stirring, and 0.17 g of 0.1 M HCl was added. After 10 minutes, 0.21 g of 20% $NH_3$ solution was added. The mixture was stirred for 24 hours and then centrifuged for 30 minutes at 4000 rpm, and then washed with water and centrifuged again. The powder obtained was recovered on filter paper and then air-dried.

The fluorescence of the coated pigment obtained was evaluated under a 365 nm UV lamp: the fluorescence is not enhanced in comparison with that of the uncoated pigment.

EXAMPLE 10

A nail varnish having the following composition was prepared:

| | |
|---|---|
| Nitrocellulose | 10 g |
| Plasticizers and resin | 15 g |
| Rheology agent | 1.5 g |
| Coated organic pigment of Example 1 | 10 g |
| Ethyl acetate, butyl acetate qs | 100 g |

After application of the composition to the nails, a bright red makeup film was obtained.

A similar composition is prepared with the organic pigment of Example 2 or of Example 3 or of Example 4.

The invention claimed is:

1. A process for preparing a coated organic pigment, comprising the following steps:
   a) an anhydrous mixture
      (i) of an organic pigment and (ii) of a siliceous compound of formula (I):

$$[R_1-O]_3Si-R_2 \quad (I)$$

in which $R_1$ denotes a $C_1$-$C_4$ alkyl radical and $R_2$ denotes a $C_1$-$C_8$ alkyl radical;
   is prepared, optionally in the presence of less than 9.5% by weight of tetra($C_1$-$C_4$) alkyl orthosilicate;
   and optionally (iii) of an oil;
   b) said mixture is placed in contact with an aqueous composition comprising a surfactant chosen from ($C_8$-$C_{16}$) alkyl sulfate salts and oxyethylenated ($C_6$-$C_{10}$)alkylphenols comprising from 5 to 40 ethylene oxide units;
   c) the coated pigment in powder form is recovered.

2. The process as claimed in claim 1, wherein the organic pigment is chosen from:
   cochineal carmine,
   organic pigments of azo dyes, anthraquinone dyes, indigoid dyes, xanthene dyes, pyrene dyes, quinoline dyes, triphenylmethane dyes or fluoran dyes;
   organic lakes or insoluble sodium, potassium, calcium, barium, aluminum, zirconium, strontium or titanium salts of acidic azo, anthraquinone, indigoid, xanthene, pyrene, quinoline, triphenylmethane or fluoran dyes;
   D&C Red No. 7;
   curcumin, riboflavin, azorubin, amaranth, chlorophyll, carotenoid, anthocyan, sorghum or carminic acid lakes.

3. The process as claimed in claim 1, wherein the organic pigment is D&C Red No. 7.

4. The process as claimed in claim 1, wherein, for the siliceous compound (I), $R_1$ denotes a $C_2$-$C_3$ alkyl radical and $R_2$ denotes a $C_1$-$C_4$ alkyl radical.

5. The process as claimed in claim 4, wherein the siliceous compound (I) is methyltriethoxysilane.

6. The process as claimed in claim 4, wherein the organic pigment is present in the anhydrous mixture in a content ranging from 0.49% to 34% by weight, relative to the total weight of the anhydrous mixture.

7. The process as claimed in claim 4, wherein the siliceous compound (I) is present in the anhydrous mixture in a content ranging from 33% to 99.5% by weight, relative to the total weight of the anhydrous mixture.

8. The process as claimed in claim 7, wherein the organic pigment and the siliceous compound (I) are used in an organic pigment/siliceous compound (I) weight ratio ranging from 0.08 to 1.

9. The process as claimed in claim 1, wherein the oil optionally present is an apolar oil.

10. The process as claimed in claim 9, wherein the surfactant is chosen from sodium lauryl sulfate and ethoxylated octylphenol containing from 5 to 40 ethylene oxide units.

11. The process as claimed in claim 1, wherein the surfactant is present in the aqueous composition in a content ranging from 0.1% to 5% by weight relative to the total weight of the aqueous composition.

12. The process as claimed in claim 2, wherein, for the siliceous compound (I), $R_1$ denotes a $C_2$-$C_3$ alkyl radical and $R_2$ denotes a $C_1$-$C_4$ alkyl radical.

13. The process as claimed in claim 3, wherein, for the siliceous compound (I), $R_1$ denotes a $C_2$-$C_3$ alkyl radical and $R_2$ denotes a $C_1$-$C_4$ alkyl radical.

14. The process as claimed in claim 5, wherein the organic pigment is present in the anhydrous mixture in a content ranging from 0.49% to 34% by weight, relative to the total weight of the anhydrous mixture.

15. The process as claimed in claim 4, wherein the siliceous compound (I) is present in the anhydrous mixture in a content ranging from 33% to 99.5% by weight, relative to the total weight of the anhydrous mixture.

16. The process as claimed in claim 14, wherein the siliceous compound (I) is present in the anhydrous mixture in a content ranging from 33% to 99.5% by weight, relative to the total weight of the anhydrous mixture; wherein the organic pigment and the siliceous compound (I) are used in an organic pigment/siliceous compound (I) weight ratio ranging from 0.08 to 1 and wherein the surfactant is present in the aqueous composition in a content ranging from 0.1% to 5% by weight relative to the total weight of the aqueous composition.

17. The process as claimed in claim 16, wherein the siliceous compound (I) is methyltriethoxysilane.

18. The process as claimed in claim 17, wherein the organic pigment is D&C Red No. 7.

19. The process as claimed in claim 16, wherein the surfactant is present in the aqueous composition in a content ranging from 0.2% to 1.5% by weight relative to the total weight of the aqueous composition.

20. The process as claimed in claim 1, wherein the surfactant is present in the aqueous composition in a content ranging from 0.2% to 1.5% by weight relative to the total weight of the aqueous composition.

* * * * *